US00PP15195P2

(12) United States Plant Patent
Olesen et al.

(10) Patent No.: US PP15,195 P2
(45) Date of Patent: Sep. 28, 2004

(54) ROSE PLANT NAMED 'POULHT001'

(50) Latin Name: *Rosa hybrida*
Varietal Denomination: POULht001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,877

(22) Filed: Dec. 16, 2003

(51) Int. Cl.[7] ..... A01H 5/00
(52) U.S. Cl. ..... Plt./133
(58) Field of Search ..... Plt./133, 137, 130

*Primary Examiner*—Anne Marie Grunberg
*Assistant Examiner*—June Hwu

(57) ABSTRACT

A new garden rose plant of the hybrid tea class which has abundant, white to light pink flowers, a unique perfumed scent, and attractive foliage. This new and distinct variety has shown to be uniform and stable in the resulting generations from asexual propagation.

2 Drawing Sheets

Botanical classification: *Rosa hybrida.*
Variety denomination: 'POULht001'.

SUMMARY OF THE INVENTION

The present invention constitutes a new and distinct variety of garden rose plant which originated from a controlled crossing between the female parent, an unnamed seedling, and the male pollen parent 'POULduce', described and illustrated in U.S. Plant patent application No. 10/237,266 dated Sep. 4, 2002 now abandoned. The two parents were crossed during the summer of 1993 and the resulting seeds were planted in a controlled environment in Fredensborg, Denmark. The new variety is named 'POULht001'.

The new variety may be distinguished from its unnamed female seed parent, by the following combination of characteristics:

1. While the seed parent has mild fragrance, 'POULht001' has a very strong fragrance.
2. While the seed parent has a Yellow-Green flower bud color, the same of 'POULht001' is White with light pink intonations.
3. While the seed parent has few petaloids, 'POULht001' has many.

The new variety may be distinguished from its male pollen parent, 'POULduce' by the following combination of characteristics:

1. While 'POULduce' has an open flower color of Yellow Group 3C–4D, the same of 'POULht001' is White Group 155B.
2. 'POULduce' has an open flower diameter of 100 to 130 mm. The flower diameter of 'POULht001' is 80 mm.
3. The pollen parent has 50 to 65 flower petals. 'POULht001' has only 25 to 30 petals.

The objective of the hybridization of this rose variety was to create a new and distinct variety for garden use with unique qualities, such as:

1. Uniform and abundant white to light pink flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULht001' from all other varieties of which we are aware.

As part of their rose development program, L. Pernille Olesen and Mogens N. Olesen germinated the seeds from the aforementioned hybridization during winter of 1993 and conducted evaluations on the resulting seedlings in a controlled environment in Fredensborg, Denmark.

'POULht001' was selected in the spring 1994 by the inventors as a single plant from the progeny of the aforementioned hybridization.

Asexual reproduction of 'POULht001' by traditional budding and rooted cuttings was first done by L. Pernille and Mogens N. Olesen in their nursery in Fredensborg, Denmark in July, 1994. This initial and other subsequent asexual propagations conducted in controlled environments has demonstrated that the characteristics of 'POULht001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULht001'.

Specifically illustrated in SHEET 1:

FIG. 1.1; Open flower showing attachment of leaves and peduncle;

FIG. 1.2; Flower buds closed;

FIG. 1.3; Flower petals, detached;

FIG. 1.4; Sepals, receptacle, and peduncle;

Specifically illustrated in SHEET 2:

FIG. 2.1; Juvenile leaves detached, juvenile leaves attached to stem;

FIG. 2.2; Bare stem exhibiting thorns;

FIG. 2.3; Mature leaf.

DETAILED DESCRIPTION OF THE VARIETY

The following is a description of 'POULht001', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULheart', a rose variety from the same inventors described and illustrated in U.S. Plant patent application No. 09/270,179 dated Mar. 15, 1999, now abandoned, are compared to 'POULht001' in Chart 1.

CHART 1

| | 'POULht001' | 'POULheart' |
|---|---|---|
| Petal count | 25 to 30 | 38 to 42 |
| Open flower diameter | 80 mm | 90 to 120 mm |
| Petal spot coloration: outermost petals after opening | Outer and Inner side: Light intonations of Yellow Group 4C | Outer Side: Green-Yellow Group 1D. Inner Side: Yellow Group 3B. |
| General tonality | On open flower White Group 155B. No change in the general tonality at the end of the 10th day. | On open flower Yellow-White Group 158B. No change in the general tonality at the end of the 4th day. Afterwards, general tonality is White Group 155D. |

FLOWER AND FLOWER BUD

Blooming habit: Recurrent.

Flower bud:

*Size.*—Upon opening, 45 mm in length from base of receptacle to end of bud.

*Bud form.*—Pointed ovoid.

*Bud color.*—As sepals unfold, petals are White Group 155C with intonations of Red Group 39D.

*Sepals.*—Upper Surface: Color: Yellow-Green Group 145B with intonations of Greyed-Red Group 181A. Texture: Moderately pubescent. Lower Surface: Color: Yellow-Green Group 144A with intonations of Greyed-Red Group 181A. Texture: Smooth. Very few stipitate glands. Sepal Shape: Sepal apex is cirrhose. Base is flat at union with receptacle. Margin: Medium foliaceous appendages on three of the five sepals. Size: 30 mm (l)×10 mm (w).

*Receptacle.*—Surface: Smooth and glabrous. Shape: Urn-shaped. Size: 9 mm (h)×12 mm (w). Color: Yellow-Green Group 144B.

*Peduncle.*—Surface: Smooth. Length: 70 to 75 mm average length. Color: Yellow-Green Group 144B. Anthocyanin: Very light intonations of Greyed-Red Group 181A. Strength: Strong.

*Borne.*—Singularly.

Flower bloom:

*Fragrance.*—Strong fragrance of old rose with lemon and grapefruit overtones.

*Duration.*—The blooms have a duration on the plant of approximately 8 to 10 days. Afterwards, petals fall cleanly away from plant.

*Size.*—Average flower diameter is 80 mm when open.

*Form.*—Traditional hybrid tea shape.

*Shape of flower when viewed from the side.*—Upon opening, upper part: Flat. Upon opening, lower part: Convex. Open flower, upper part: Flat. Open flower, lower part: Concave.

*Petalage.*—Average range: 25 to 30 petals under normal conditions with 6 petaloids.

Color:

*Upon opening, petals.*—Outermost petals: Outer side: White Group 155B with intonations of Red Group 39D. Inner Side: White Group 155B with intonations of Red Group 39D. Innermost petals: Outer side: White Group 155B with faint intonations of Red Group 39D. Inner Side: White Group 155B.

*Upon opening, basal petal spots.*—Outermost petals: Outer side: Light intonations of Yellow Group 4C. Inner Side: Light intonations of Yellow Group 4C. Innermost petals: Outer side: Light intonations of Yellow Group 4C. Inner Side: Light intonations of Yellow Group 4C.

*After opening, petals.*—Outermost petals: Outer side: White Group 155B. Inner Side: White Group 155B. Innermost petals: Outer side: White Group 155B. Inner Side: White Group 155B.

*After opening, basal petal spots.*—Outermost petals: Outer side: Light intonations of Yellow Group 4C. Inner Side: Light intonations of Yellow Group 4C. Innermost petals: Outer Side: Light intonations of Yellow Group 4C. Inner Side: Light intonations of Yellow Group 4C.

General tonality: On open flower White Group 155B. No change in the general tonality at the end of the 10th day. Afterwards, general tonality remains the same.

Petals:

*Petal reflex.*—Strong.

*Margin.*—Entire. Medium undulations of margin.

*Shape.*—Petal apex is round. Petal base is acute.

*Size.*—55 mm (l)×55 mm (w).

*Texture.*—Smooth.

*Thickness.*—Thick.

*Arrangement.*—Not Formal.

Petaloids:

*Quantity.*—4 to 6.

*Color.*—Upper Surface: White Group 155B. Lower Surface: White Group 155B with light intonations of Red Group 39D.

*Size.*—50 mm (l)×20 mm (w).

Reproductive organs:

*Pistils.*—Length: 4 mm. Quantity: 107 (actual count).

*Pollen.*—Color: None observed.

*Anthers.*—Size: 3 mm in length. Color: Greyed-Orange Group 163A. Quantity: 193 (actual count).

*Filaments.*—Color: White Group 155B with intonations of Greyed-Red Group 181C. Length: 15 mm.

*Stigmas.*—Inferior relative to the height and length of the anthers. Color: Greyed-Yellow Group 162C.

*Styles.*—Color: Red-Purple Group 57A to 60A.

*Hips.*—None Observed in the field nursery in Jackson County Oreg.

PLANT

Plant growth: Moderate, upright to bushy. When grown as a budded field grown plant on *Rosa multiflora* understock, the average height of the plant is 100 to 150 cm and the average width is 100 cm.

Stems:

*Color.*—Young wood: Yellow-Green Group 145B. Strong intonations of anthocyanic pigment the color of Greyed-Purple Group 185B. Older wood: Yellow-Green Group 144A. Surface Texture: Young wood: Rough, with very fragrant stipitate glands. Older wood: Smooth. Anthocyanin: Greyed-Purple Group 185B occurring with stipitate glands.

Thorns:

*Incidence.*—7 thorns per 10 cm of stem.

*Size.*—8 mm.

*Color.*—Yellow-Green Group 145B with varying intonations of Greyed-Purple Group 184A.

*Shape.*—Deeply concave.

Plant foliage: Normal number of leaflets on leaves in middle of the stem: 5 leaflets.

*Compound leaf size.*—150 mm (l)×120 mm (w).

*Quantity.*—Very.

*Color.*—Mature Foliage: Upper Leaf Surface: Yellow-Green Group 147A. Lower Leaf Surface: Yellow-Green Group 148B. Juvenile foliage: Upper Leaf Surface: Greyed-Purple Group 183A. Lower Leaf Surface: Greyed-Purple Group 183C.

Plant leaves and leaflets:

*Stipules.*—Size: 25 mm. Color: Yellow-Green Group 144B. Margins: Finely serrated with stipitate glands.

*Petiole.*—Length: 30 mm. Color: Yellow-Green Group 144B. Anthocyanin: Greyed-Purple Group 184B. Underneath: Prickles. Margins: Stipitate glands observed.

*Rachis.*—Length: 30 mm. Color: Yellow-Green Group 144B. Anthocyanin: Greyed-Purple Group 184B. Underneath: Prickles. Margins: Stipitate glands observed.

*Leaflet.*—Size: 70 to 80 mm (l)×45 to 55 mm (w). Edge: Finely serrated. Shape: Generally ovate. The shape of the apex is cuspidate. Base shape is rounded. Texture: Smooth. Arrangement: Odd pinnate. Venation: Reticulate. Glossiness: Very glossy.

Disease resistance: Above average resistance to mildew, rust, black spot, and Botrytis under normal growing conditions in Jackson County, Oreg.

Cold hardiness: The variety 'POULht001' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant white to light pink flowers, strong fragrance, disease resistance, and extended period of bloom.

* * * * *

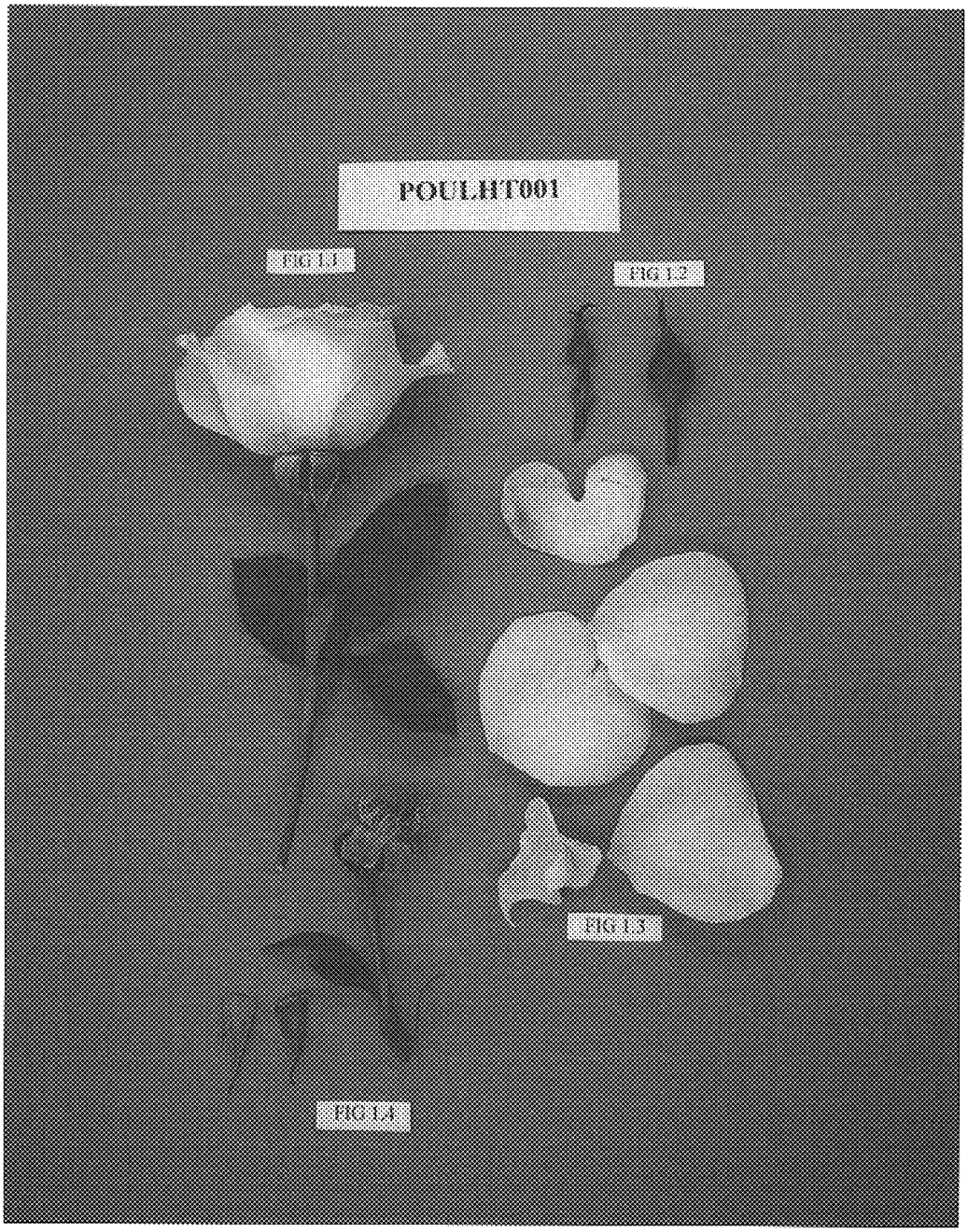
POULHT001
FIG 1.1
FIG 1.2
FIG 1.3
FIG 1.4

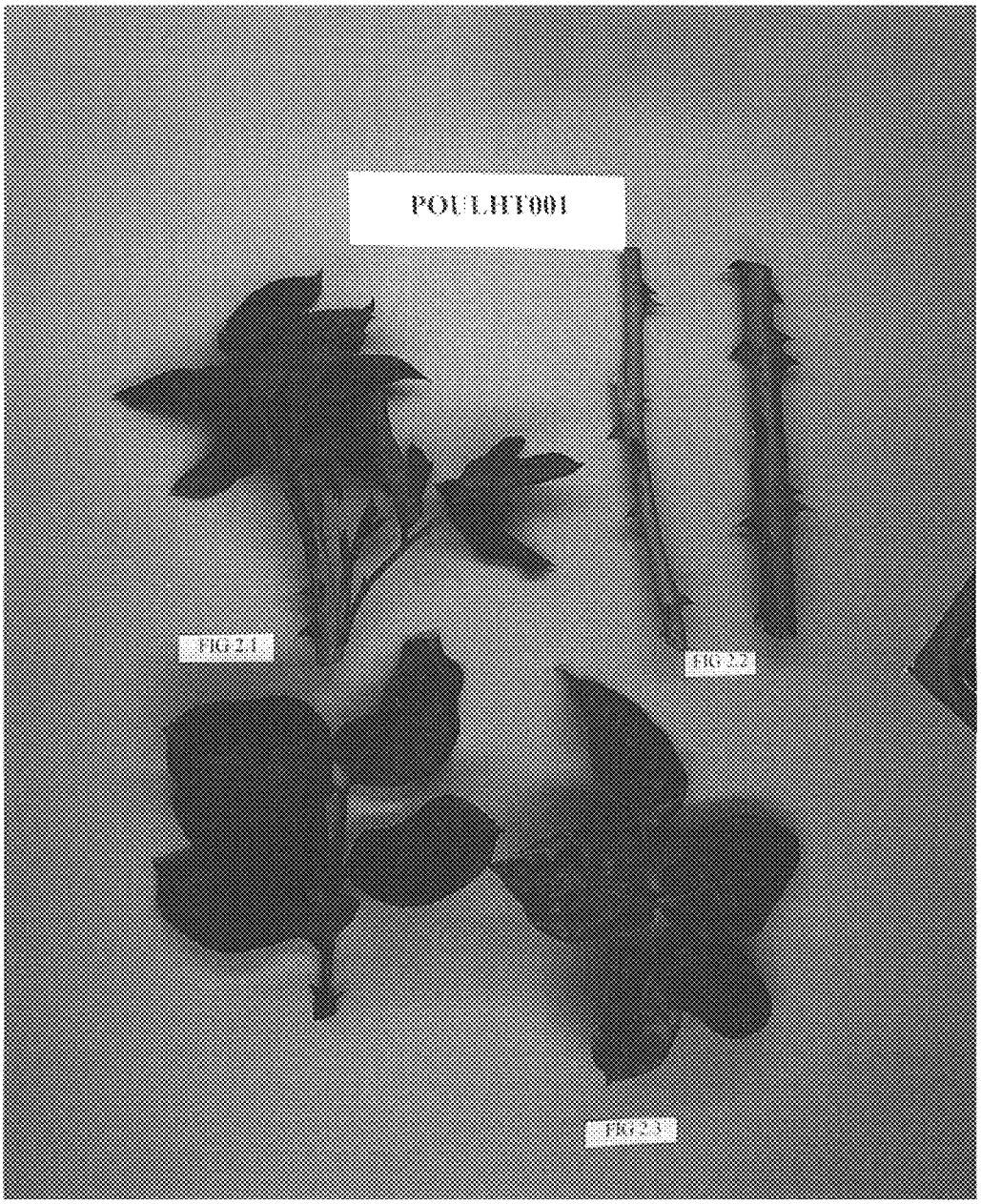
POULHT001
FIG 2.1
FIG 2.2
FIG 2.3